(12) United States Patent
Capote et al.

(10) Patent No.: US 8,328,871 B2
(45) Date of Patent: Dec. 11, 2012

(54) EXPANDING VERTEBRAL BODY IMPLANT

(75) Inventors: Marco D. Capote, Memphis, TN (US); Keith E. Miller, Germantown, TN (US); Dean G. Karahalios, Lake Forest, IL (US); Eric A. Potts, Indianapolis, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1342 days.

(21) Appl. No.: 11/558,320

(22) Filed: Nov. 9, 2006

(65) Prior Publication Data
US 2008/0114467 A1 May 15, 2008

(51) Int. Cl.
A61F 2/44 (2006.01)
(52) U.S. Cl. .................................... 623/17.16
(58) Field of Classification Search .... 623/17.11–17.16; 403/109.1–109.8
See application file for complete search history.

(56) References Cited

U.S. PATENT DOCUMENTS

| | | | |
|---|---|---|---|
| 4,157,715 A | 6/1979 | Westerhoff | |
| 4,180,346 A * | 12/1979 | Blake | 403/109.3 |
| 4,401,112 A | 8/1983 | Rezaian | |
| 4,657,550 A | 4/1987 | Daher | |
| 4,820,305 A | 4/1989 | Harms | |
| 4,932,975 A | 6/1990 | Main et al. | |
| 5,026,373 A | 6/1991 | Ray et al. | |
| 5,062,850 A | 11/1991 | MacMillan et al. | |
| 5,281,226 A | 1/1994 | Davydov et al. | |
| 5,336,223 A | 8/1994 | Rogers | |
| 5,571,190 A | 11/1996 | Ulrich et al. | |
| 5,571,192 A | 11/1996 | Schonhoffer | |
| 5,702,451 A | 12/1997 | Biedermann | |
| 5,702,453 A | 12/1997 | Rabbe et al. | |
| 5,702,455 A | 12/1997 | Saggar | |
| 5,723,013 A | 3/1998 | Jeanson et al. | |
| 5,776,197 A | 7/1998 | Rabbe et al. | |
| 5,776,198 A | 7/1998 | Rabbe et al. | |
| 5,989,290 A | 11/1999 | Biedermann et al. | |
| 6,015,436 A * | 1/2000 | Schonhoffer | 623/17.16 |
| 6,086,613 A | 7/2000 | Camino et al. | |
| 6,159,244 A | 12/2000 | Suddaby | |
| 6,176,881 B1 * | 1/2001 | Schar et al. | 623/17.11 |
| 6,190,413 B1 | 2/2001 | Sutcliffe | |

(Continued)

FOREIGN PATENT DOCUMENTS
DE 4012622 C1 7/1991
(Continued)

OTHER PUBLICATIONS
Unpublished U.S. Appl. No. 11/412,441, filed Apr. 27, 2006 titled "Expandable Vertebral Implant and Methods of Use".

Primary Examiner — Thomas Barrett
Assistant Examiner — Matthew Lawson (57) ABSTRACT

An expandable medical implant for supporting bone structures is disclosed. The implant may include an outer member and an inner member receivable in the outer member. One of the outer and inner members includes a tapered surface and the other of the outer and inner members includes a scalloped surface. The implant may also include a locking element disposed between the tapered surface and the scalloped surface. The tapered surface may be movable relative to the locking element to transversely shift the locking element into engagement with the scalloped surface to inhibit a decrease in the overall implant height.

34 Claims, 5 Drawing Sheets

U.S. PATENT DOCUMENTS

| | | | | |
|---|---|---|---|---|
| 6,193,755 | B1 | 2/2001 | Metz-Stavenhagen et al. | |
| 6,193,756 | B1* | 2/2001 | Studer et al. | 623/17.15 |
| 6,200,348 | B1* | 3/2001 | Biedermann et al. | 623/17.11 |
| 6,296,665 | B1 | 10/2001 | Strnad et al. | |
| 6,332,895 | B1 | 12/2001 | Suddaby | |
| 6,344,057 | B1 | 2/2002 | Rabbe et al. | |
| 6,352,556 | B1 | 3/2002 | Kretschmer et al. | |
| 6,395,034 | B1 | 5/2002 | Suddaby | |
| 6,454,806 | B1 | 9/2002 | Cohen et al. | |
| 6,524,341 | B2* | 2/2003 | Lang et al. | 623/17.15 |
| 6,562,074 | B2 | 5/2003 | Gerbec et al. | |
| 6,616,695 | B1* | 9/2003 | Crozet et al. | 623/17.11 |
| 6,648,917 | B2 | 11/2003 | Gerbec et al. | |
| 6,719,796 | B2 | 4/2004 | Cohen et al. | |
| 6,730,088 | B2* | 5/2004 | Yeh | 606/247 |
| 6,866,682 | B1 | 3/2005 | An et al. | |
| 6,991,653 | B2 | 1/2006 | White et al. | |
| 7,156,874 | B2 | 1/2007 | Paponneau et al. | |
| 7,311,733 | B2* | 12/2007 | Metz-Stavenhagen | 623/17.15 |
| 7,544,208 | B1* | 6/2009 | Mueller et al. | 623/17.15 |
| 2002/0161441 | A1* | 10/2002 | Lang et al. | 623/17.11 |
| 2003/0163199 | A1 | 8/2003 | Boehm et al. | |
| 2003/0181980 | A1 | 9/2003 | Berry et al. | |
| 2003/0191531 | A1 | 10/2003 | Berry et al. | |
| 2003/0208272 | A1 | 11/2003 | Crozet et al. | |
| 2004/0073314 | A1 | 4/2004 | White et al. | |
| 2004/0153160 | A1 | 8/2004 | Carrasco | |
| 2004/0186569 | A1 | 9/2004 | Berry | |
| 2005/0060036 | A1* | 3/2005 | Schultz et al. | 623/17.15 |
| 2005/0090898 | A1 | 4/2005 | Berry et al. | |
| 2005/0096744 | A1* | 5/2005 | Trieu et al. | 623/17.11 |
| 2005/0113921 | A1* | 5/2005 | An et al. | 623/17.11 |
| 2005/0159814 | A1 | 7/2005 | Karahalios | |
| 2005/0187634 | A1 | 8/2005 | Berry | |
| 2005/0209697 | A1 | 9/2005 | Paponneau et al. | |
| 2005/0234550 | A1* | 10/2005 | Metz-Stavenhagen | 623/17.11 |
| 2006/0058879 | A1* | 3/2006 | Metz-Stavenhagen | 623/17.15 |
| 2006/0100710 | A1* | 5/2006 | Gutlin et al. | 623/17.15 |
| 2006/0116770 | A1 | 6/2006 | White et al. | |
| 2006/0200244 | A1* | 9/2006 | Assaker | 623/17.15 |
| 2006/0241762 | A1* | 10/2006 | Kraus | 623/17.11 |
| 2007/0028710 | A1* | 2/2007 | Kraus et al. | 74/400 |
| 2007/0123987 | A1* | 5/2007 | Bernstein | 623/17.11 |
| 2007/0191954 | A1* | 8/2007 | Hansell et al. | 623/17.15 |
| 2007/0250171 | A1* | 10/2007 | Bonin, Jr. | 623/17.15 |
| 2007/0255408 | A1* | 11/2007 | Castleman et al. | 623/17.11 |
| 2007/0255409 | A1* | 11/2007 | Dickson et al. | 623/17.11 |
| 2007/0255410 | A1* | 11/2007 | Dickson et al. | 623/17.11 |
| 2007/0255421 | A1* | 11/2007 | Dickson | 623/23.47 |
| 2007/0270964 | A1* | 11/2007 | Strohkirch et al. | 623/17.11 |
| 2008/0004705 | A1* | 1/2008 | Rogeau et al. | 623/17.16 |
| 2008/0009946 | A1* | 1/2008 | Douget et al. | 623/17.16 |
| 2008/0264196 | A1* | 10/2008 | Schindler et al. | 74/493 |
| 2008/0281424 | A1* | 11/2008 | Parry et al. | 623/17.16 |
| 2008/0288071 | A1* | 11/2008 | Biyani et al. | 623/17.11 |
| 2009/0138083 | A1* | 5/2009 | Biyani | 623/17.11 |

FOREIGN PATENT DOCUMENTS

| | | |
|---|---|---|
| DE | 19509317 A1 | 9/1996 |
| DE | 19804765 A1 | 9/2000 |
| DE | 20213013 U1 | 1/2003 |
| EP | 0490159 A1 | 6/1992 |
| EP | 1080703 A2 | 3/2001 |
| EP | 1188424 A1 | 3/2002 |
| FR | 2636227 A1 | 11/2007 |
| WO | WO9201428 A1 | 2/1992 |
| WO | WO9846173 A1 | 10/1998 |
| WO | WO9939665 A1 | 8/1999 |
| WO | WO9963913 A2 | 12/1999 |
| WO | WO0023013 A1 | 4/2000 |
| WO | WO0045751 A1 | 8/2000 |
| WO | WO02071986 A2 | 9/2002 |
| WO | WO03096937 A1 | 5/2003 |
| WO | WO2004089256 A1 | 10/2004 |
| WO | WO2004100837 A1 | 11/2004 |

\* cited by examiner

EXPANDING VERTEBRAL BODY IMPLANT

FIELD OF THE INVENTION

The present invention relates generally to the field of replacing portions of the human structural anatomy with medical implants, and more particularly relates to an expandable implant and method for replacing bone structures such as one or more vertebrae or long bones.

BACKGROUND

Figure 1:
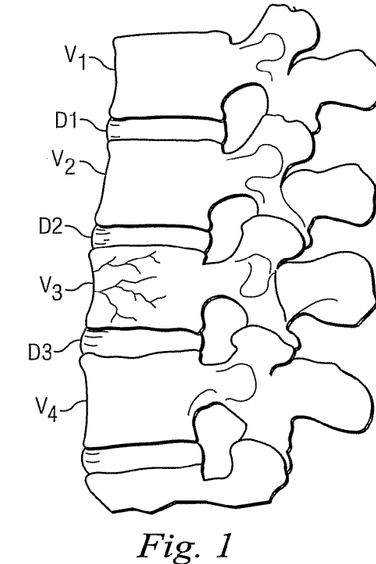
FIG. 1 is an elevation view of a segment of a lumbar spine.

It is sometimes necessary to remove one or more vertebrae, or a portion of the vertebrae, from the human spine in response to various pathologies. For example, one or more of the vertebrae may become damaged as a result of tumor growth, or may become damaged by a traumatic or other event. Excision of at least a generally anterior portion, or vertebral body, of the vertebra may be referred to as a corpectomy. An implant is usually placed between the remaining vertebrae to provide structural support for the spine as a part of a corpectomy. FIG. 1 illustrates four vertebrae, $V_1$-$V_4$ of a typical lumbar spine and three spinal discs, $D_1$-$D_3$. As illustrated, $V_3$ is a damaged vertebra and all or a part of $V_3$ could be removed to help stabilize the spine. If removed along with spinal discs $D_2$ and $D_3$, an implant may be placed between vertebrae $V_2$ and $V_4$. Most commonly, the implant inserted between the vertebrae is designed to facilitate fusion between remaining vertebrae. Sometimes the implant is designed to replace the function of the excised vertebra and discs. All or part of more than one vertebrae may be damaged and require removal and replacement in some circumstances.

Many implants are known in the art for use in a corpectomy procedure. One class of implants is sized to directly replace the vertebra or vertebrae that are being replaced. Another class of implants is inserted into the body in a collapsed state and then expanded once properly positioned. Expandable implants may be advantageous because they allow for a smaller incision when properly positioning an implant. Additionally, expandable implants may assist with restoring proper loading to the anatomy and achieving more secure fixation of the implant. Implants that include insertion and expansion members that are narrowly configured may also provide clinical advantages. In some circumstances, it is desirable to have vertebral endplate contacting surfaces that effectively spread loading across the vertebral endplates. Effective implants should also include a member for maintaining the desired positions, and in some situations, being capable of collapsing. Fusion implants with an opening may also be advantageous because they allow for vascularization and bone growth through all or a portion of the entire implant.

Expandable implants may also be useful in replacing long bones or portions of appendages such as the legs and arms, or a rib or other bone that is generally longer than it is wide. Examples include, but are not limited to, a femur, tibia, fibula, humerus, radius, ulna, phalanges, clavicle, and any of the ribs.

SUMMARY

In one exemplary aspect, an expandable medical implant for supporting bone structures is disclosed. The implant has an overall implant height adjustable along a longitudinal axis. The implant may include an outer member configured to cooperatively engage a first bone structure and an inner member receivable in the outer member. The inner member may be movable relative to the outer member to increase and decrease the overall implant height. The inner member may be configured to cooperatively engage a second bone structure. One of the outer and inner members includes a tapered surface and the other of the outer and inner members includes a scalloped surface. The implant may also include a locking element disposed between the tapered surface and the scalloped surface. The tapered surface may be movable relative to the locking element to transversely shift the locking element into engagement with the scalloped surface to inhibit a decrease in the overall implant height.

In another exemplary aspect, a locker member may be disposed between the inner and outer member. The locker member may include a receiving aperture containing the locking element, and may be configured to act on the locking element to affect the position of the locking element relative to the outer member. The tapered surface of the outer member may be configured to affect the position of the locking element relative to the scalloped surface of the inner member.

In another exemplary aspect, an expandable medical implant for supporting bone structures may include an outer member having an inner surface configured to cooperatively engage a first bone structure. The implant also may include an inner member receivable in the outer member and movable relative to the outer member to increase and decrease the overall implant height. The inner member may have a scalloped surface and may be configured to cooperatively engage a second bone structure. A locking element may be disposed between the inner surface of the outer member and the scalloped surface of the inner member. The locking element may be movable between a locked condition and an unlocked condition and may be biased toward the locked condition. The locking element may be disposed to selectively engage the scalloped surfaces to inhibit a decrease in the overall implant height.

In another exemplary aspect, the implant may include a locker member disposed between the inner and outer member, the locker member including a receiving aperture containing the locking element.

In yet another exemplary aspect, an expandable medical implant for supporting bone structures may include an outer member having a tapered inner surface and being configured to cooperatively engage a first bone structure. The implant also may include a locker member receivable in the outer member and movable relative to the outer member. The locker member may include a receiving aperture. An inner member may be receivable in the locker member and movable relative to the locker member and the outer member to increase and decrease the overall implant height. The inner member may have a scalloped surface and may be configured to cooperatively engage a second bone structure. A locking element may be disposed within the receiving aperture of the locker member. The locking element may be associated with the tapered inner surface of the outer member and the scalloped surface of the inner member. The tapered surface may be movable relative to the locking element to transversely shift the locking element into engagement with the scalloped surface to inhibit a decrease in the overall implant height.

In yet another exemplary aspect, a method of supporting bone structures with an expandable medical implant is disclosed. The implant may have an overall implant height adjustable along a longitudinal axis. The method may include placing the implant between bone structures to be supported and displacing an inner member having a scalloped surface relative to an outer member having a tapered inner surface in order to increase the overall implant height. The outer member may be configured to cooperatively engage a first bone structure and the inner member may be configured to cooperatively engage a second bone structure. Displacing the inner member may allow a locking element to disengage the scalloped surface. A compressive load may be supported from the bone structures on the inner and outer members, and the compressive load may cause the tapered surface to shift the locking element into engagement with the scalloped surface and to inhibit a decrease in the overall implant height.

In yet another exemplary aspect, an expandable medical implant for supporting bone structures includes an outer member being configured to cooperatively engage a first bone structure and an inner member receivable in the outer member. The inner member may be movable relative to the outer member to increase and decrease the overall implant height and may be configured to cooperatively engage a second bone structure. At least one of the inner and outer members includes vascularization openings formed on first and second opposing sides of the implant. The vascularization openings on the first opposing side may be larger than the vascularization openings on the second opposing side.

Further aspects, forms, embodiments, objects, features, benefits, and advantages of the present invention shall become apparent from the detailed drawings and descriptions provided herein.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
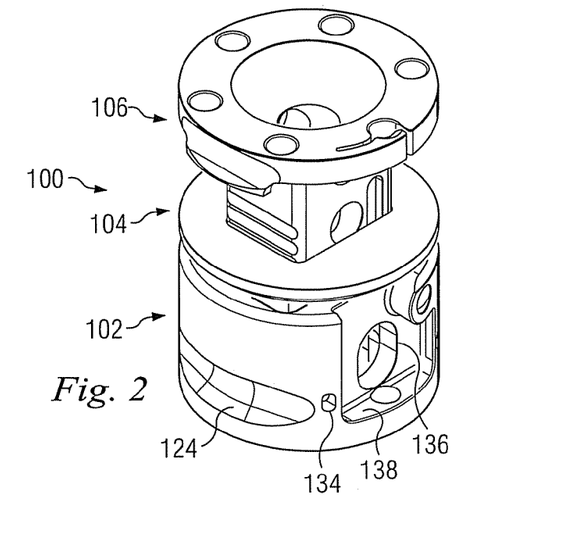
FIG. 2 is a pictorial illustration of an exemplary expandable implant according to one embodiment of the present invention.
Figure 3A:
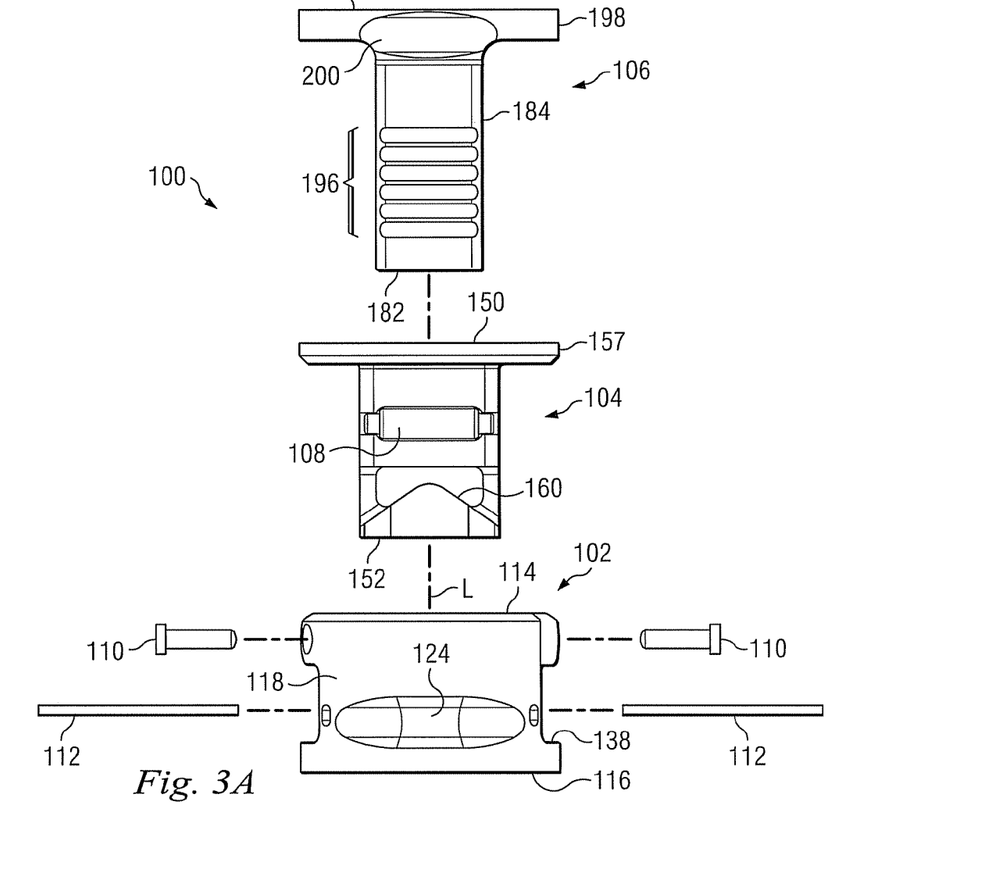
FIGS. 3a-3c are pictorial illustrations of exploded views of the implant of FIG. 2.
Figure 3B:
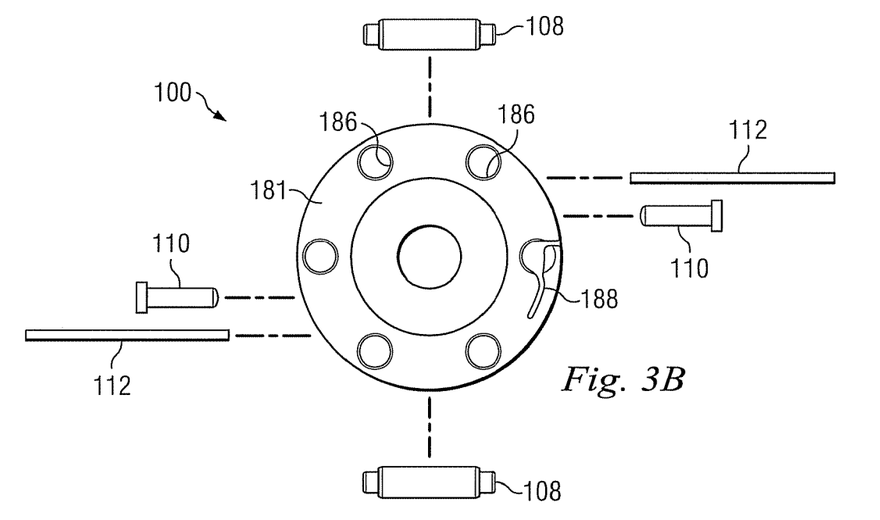
Figures 3C, 4:
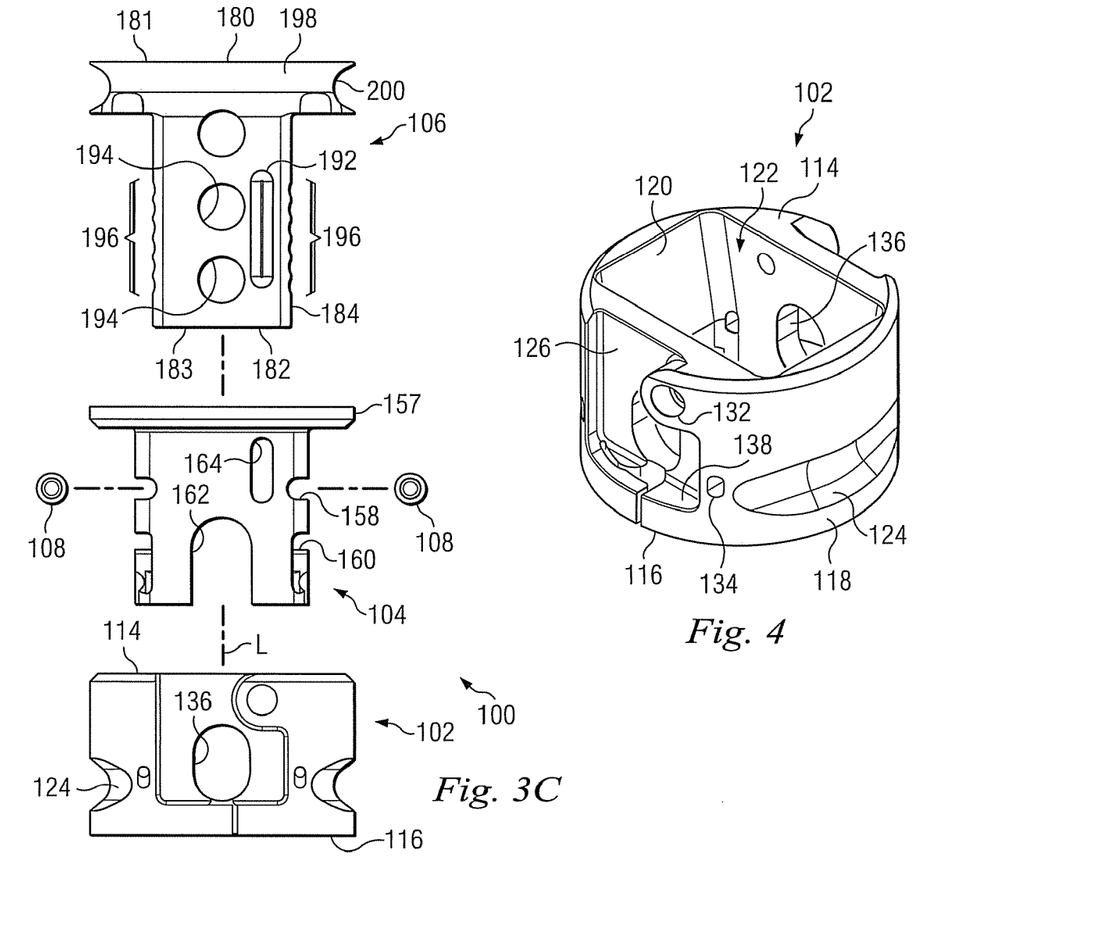
FIG. 4 is an isometric pictorial illustration of a base component of the implant of FIG. 2.

FIGS. 2 and 3a-3c show an exemplary expandable implant 100 usable to secure and space adjacent bone structures. In FIG. 2, the implant 100 is shown fully assembled, while FIGS. 3a-3c show the implant 100 in an exploded condition, along a longitudinal axis L. Referring to these figures, the implant 100 includes three main components, including a base 102, a locker 104, and a post 106. These main components operate together to provide the support and spacing between the adjacent bone structures. In addition to these components, the exemplary implant 100 includes locking elements 108, pegs 110, and biasing elements 112.

In the exemplary embodiment shown in FIGS. 2 and 3a-3c, the base 102 is configured and shaped to receive and house the locker 104, which, in turn, is configured and shaped to receive and house the post 106. The locking elements 108 cooperate with the locker 104 to control displacement of the post 106 relative to the base 102, thereby controlling the overall height of the implant 100. In this embodiment, the pegs 110 connect the base 102, the locker 104, and the post 106 into a unitary mechanism. The biasing elements 112 cooperate with the base 102 and the locker 104 to bias the locker 104, and likewise the locking element 108, into a position that selectively locks or secures the post 106 relative to the base 102, thereby hindering the ability of the implant 100 to collapse after implantation. In the embodiments shown, the biasing element 112 is a leaf spring. However, the biasing element could be any type of spring, including a coil spring, or a material, such as a silicone or elastomeric bumper, or an elastic member, such as a stretchable band that may act in compression or tension.

Figure 5:
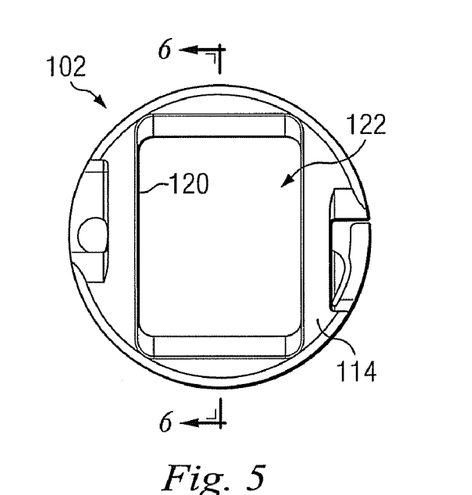
FIG. 5 is a top pictorial illustration of the base component of FIG. 4.
Figure 6:
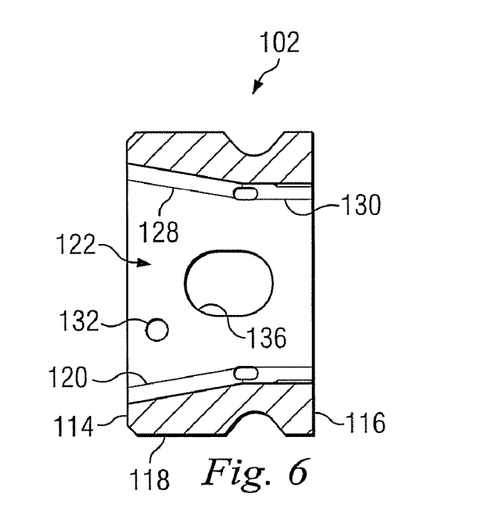
FIG. 6 is a sectional pictorial illustration of the base component of FIG. 5, taken along line 6-6.

The components of the exemplary implant 100 will be described in further detail with reference to FIGS. 4-12. The base 102 will be described first, with reference to FIGS. 4-6, as well as FIGS. 3a-3c. FIG. 4 shows an isometric view of the base 102; FIG. 5 shows a top view; and FIG. 6 shows a cross-sectional view.

The base 102 includes a top surface 114, a bottom surface 116, an outer wall 118, and an inner wall 120, defining a bore 122. The top and bottom surfaces 114, 116 may be relatively flat surfaces having the bore 122 formed therein. The top surface 114 may be configured to cooperate with locker 104, and the bottom surface 116 may be configured to cooperatively engage a bone structure, either directly or through additional components, such as endplates. The bottom surface 116 may include features for attachment to endplates or other components. Some exemplary features are described below with respect to the post 106.

In the exemplary embodiment shown, the outer wall 118 may include instrument receiving features 124 that cooperate with surgical instruments for placement of the implant 100 between desired bone structures. In the embodiment shown, the instrument receiving features 124 are indentations on opposite sides of the base outer wall 118, however, it is contemplated that many other features could be used to cooperate with instruments that would allow the instruments to grip, support, or otherwise place the implant 100 in a desired location. Further, some embodiments lack any instrument receiving features.

In the exemplary embodiment shown, in addition to the instrument receiving features 124, the outer wall 118 includes additional cut outs and features that function to reduce the mass of the implant 100 while maintaining sufficient strength to properly support the bone structures and weight of a patient. In addition, these additional cutouts and features may simplify additional processing, such as, for example, when using a wire EDM to cut features at the bottom surface 116.

Referring now to FIGS. 5 and 6, the base 102 includes the inner wall 120, forming the bore 122. In this exemplary embodiment, the bore 122 extends longitudinally from the top surface 114 through the base 102, to the bottom surface 116, as best seen in FIG. 6. As best seen in FIG. 5, the bore 122 in this exemplary embodiment is substantially rectangular. Accordingly, the inner wall 120 may be formed of substantially planar surfaces that form the rectangular shape. It should be noted that in other embodiments, the bore 122 is formed of other polygon shapes, such as, for example, triangular, square, or pentagon. Still other embodiments have bores that are oval or circular shaped. As illustrated in FIG. 2, the bore 122 is configured to receive the locker 104 of the implant 100.

The inner wall 120 has a tapered section 128 and a non-tapered section 130. In the exemplary embodiment shown, the tapered section 128 is adjacent the top surface 114 of the base 102, while the non-tapered section 130 is adjacent the bottom surface 116 of the base 102. However, the tapered section 128 may be otherwise arranged or placed. As discussed further below, the tapered section 128 cooperates with the locking element 108 to secure the height of the implant 100 at a desired level. Also, in the exemplary embodiment shown, the inner wall 120 includes two tapered sections 128, disposed on opposite sides of the bore 122. Other embodiments include one or more than two tapered sections, and for the reasons described below, symmetry may provide advantages when expanding the implant 100.

In addition to the elements described, the base 102 also includes a peg aperture 132, a biasing member aperture 134, and a vascularization aperture 136. During assembly, the peg 110 may be inserted into the peg aperture 132, and the biasing element 112 may be inserted through the biasing member aperture 134. The vascularization aperture 136 provides access to the bore 122 and may be used to introduce bone graft, tissue, or other material into the bore 122 after implantation. In addition, it allows fluid into the interior of the base 102 thereby, encouraging bone growth. Because of the cutouts, the outer wall 118 of the base 102 also forms a flange 138, as best seen in FIGS. 2, 3a, and 4.

As shown in FIG. 2, the base 102 receives the locker 104, which is described with reference to FIGS. 2, 3a-3c, and FIG. 7. The locker 104 includes an upper end 150, a lower end 152, an inner surface 154, an outer surface 156, and a flange 157.

In this exemplary embodiment and as shown in FIG. 2 in an assembled condition, the upper end 150 is disposed outside the base 102, and the lower end 152 is disposed within the bore 122 of the base 102. At the upper end 150, the flange 157 radially extends to have an outer perimeter substantially matching that of the base 102. As described below, the flange 157 may be used to displace the locker 104 relative to the base 102 in order to change the overall height of the implant 100.

Figure 7:
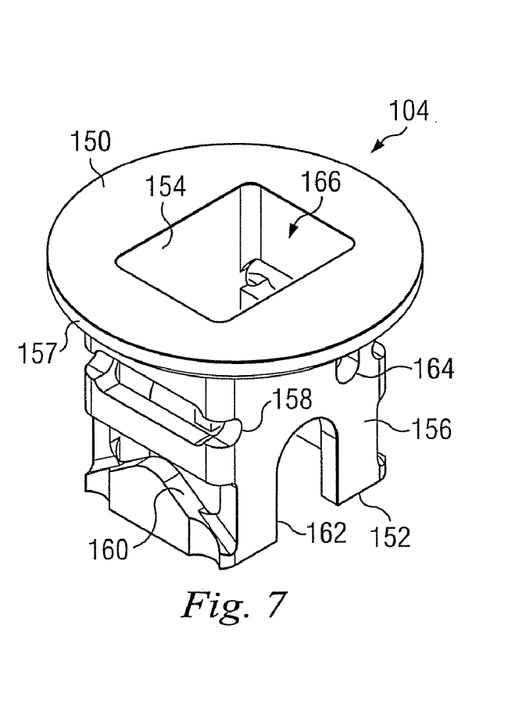
FIG. 7 is an isometric pictorial illustration of a locker component of the implant of FIG. 2.

In the embodiment shown, the outer surface 156 of the locker 104 is sized and formed to be received within the bore 122 of the base 102. In this embodiment, like the bore 122 of the base 102, the outer surface 156 is substantially rectangular. However, the outer surface may be in the form of other shapes, as described above with reference to the base 102.

The outer surface 156 includes a locking element receiver 158, which in this embodiment is an aperture from the outer surface 156 to the inner surface 154. In addition, the outer surface includes a biasing member support 160, a vascularization aperture 162, and a peg slot 164.

As described further below, the locking element 108 fits within and extends through the locking element receiver 158 to engage and disengage the base 102 and the post 106, restricting movement of the post 106 relative to the base 102. The biasing member support 160 cooperates with the biasing member 112 to provide a biasing force on the locker 104 to maintain it within the base 102. The peg slot 164 receives the peg 110, which also extends through the base 102. This allows the locker 104 to move relative to the peg 110, but the peg 110 blocks removal of the locker 104 from the base 102. Accordingly, the peg slot 164 cooperates with the peg 110 to slidably maintain the locker 104 within the base 102.

The inner surface 154 of the locker 104 forms a locker bore 166. The locker bore 166 in this exemplary embodiment is rectangular, as is the outer surface 156. However, the locker bore 166 need not be rectangular but could be formed into some other shape. As will be described below, the locker bore 166 is configured and sized to receive the post 106.

The post 106 will be described with reference to FIGS. 8 and 3a-3c. The post 106 includes a top end 180, a bottom end 182, and a main body 184 extending therebetween. The top end 180 includes a top surface 181 having end plate connectors 186 formed therein. In the embodiment shown, the end plate connectors 186 are configured for attachment to an end plate (not shown). In the embodiment shown, the end plate connectors 186 are a series of holes configured to attach to endplates. In some embodiments, instead of attaching to separate endplates, the post 106 is configured to cooperatively attach directly to bone structure. In this exemplary embodiment, one end plate connector 186 may include an attachment aid 188 that cooperates with an end plate to secure the end plate onto the top surface 180 of the post 106. In this embodiment, the attachment aid 188 is a spring feature that is deformable to receive an endplate post and frictionally grip it to hold the endplate in place during implantation. In addition, the bottom surface 116 of the base 102 may include similar features, including the end plate connectors and the attachment aid, such as the spring feature. In some embodiments, the end plate connectors are cylindrical posts that extend from an endplate and are configured to be received by the end plate connectors 186. The end plates could be at any angle or of various types. Alternatively, the end plate connectors may be used with an intermediate spacer to connect and stack two implants.

Figure 8:
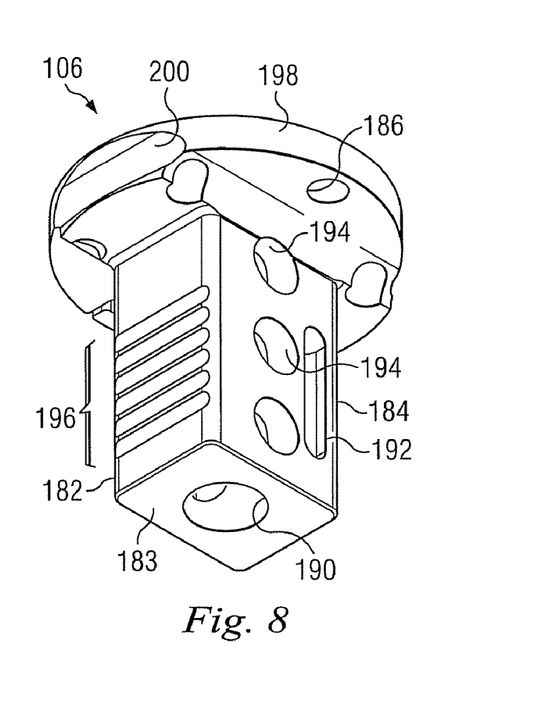
FIG. 8 is an isometric pictorial illustration of a post component of the implant of FIG. 2.

The bottom end 182 of the post 106 includes a bottom surface 183 having a vascularization aperture 190 formed therein. The bottom end 182 fits within the locker bore 166, and is slidable relative to the locker 104 and the base 102 to increase and decrease the overall height of the implant 100. In the embodiment shown, the bottom end 182 of the post 106 is sized and formed to be received within the locker bore 166. In this embodiment, like the locker bore 166, the bottom end 182 is substantially rectangular. However, the bottom end may be in the form of other shapes, as described above with reference to the base 102.

The main body 184 includes a peg slot 192, additional vascularization holes 194, and a locking surface 196. The peg slot 192 is configured to receive the peg 110, which also extends through the base 102 and locker 104. Because of the length of the peg slot 192, the post 106 may be raised or lowered relative to the peg 110 to increase or decrease the overall height of the implant 100. The vascularization holes 194 and the vascularization aperture 190 provides access for placement of bone graft or other material and allows fluid flow to promote bone growth and attachment to the bone structures.

The locking surface 196 is the area configured to contact the locking element 108, and in this exemplary embodiment, may include roughened features, such as, for example, a series of roughening scallops aligned transverse to a longitudinal axis of the implant 100, as shown in the figures. As will be described below, the roughened features, such as the scallops cooperate with the locking element 108 to secure the post at a desired height relative to the locker 104 and the base 102. In this embodiment, the scallops of the locking surface 196 are spaced less than 1 mm apart and enable an incremental increase and decrease in the height of the implant 100. A scallop radius may substantially correspond with a radius of the locking element 108, providing a relatively tight fit when the locking element is engaged with the locking surface 196. In some embodiments, the locking surface 196 is not scalloped, but includes other roughening features. For example, in some embodiments the roughened features of the locking surface includes protruding triangular features or block-like features forming teeth. Still other surface features may be simply rough surfaces, such as those formed by shot peening, blasting, etching, or machining to increase the frictional properties of the locking surface 196. Still other roughened surface features are contemplated. In yet other embodiments, the locking surface 196 is relatively smooth, thereby allowing for an infinite number of expansion increments.

In addition to the features described above, the post 106 includes a flange 198. In the exemplary embodiment shown, the flange 198 includes instrument receiving grips 200 along its outer edges, formed to fit instruments during implantation or expansion.

Figure 9:
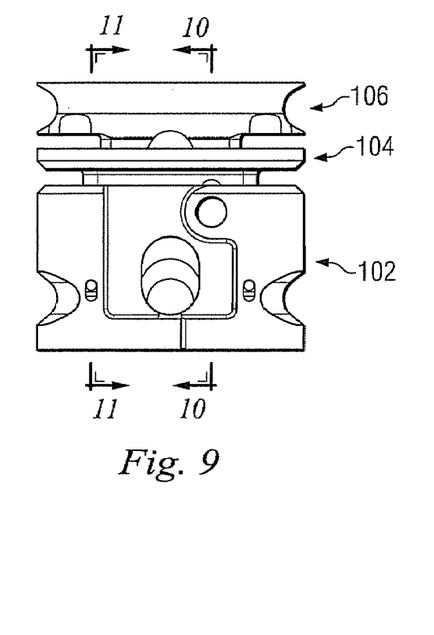
FIG. 9 is a side pictorial illustration of the implant of FIG. 2.
Figure 10:
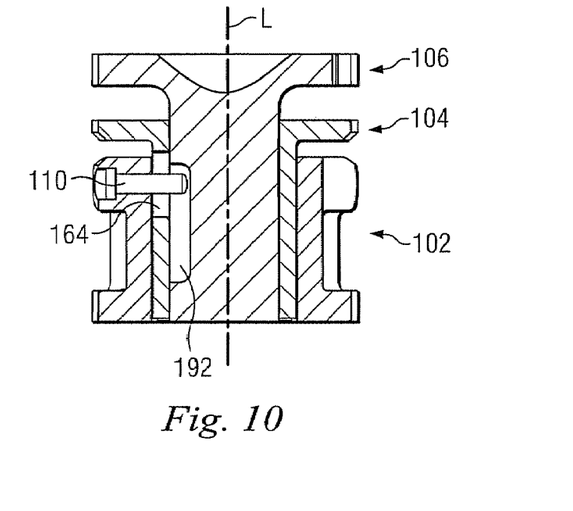
FIG. 10 is a sectional pictorial illustration taken along line 10-10 in FIG. 9.
Figure 11:
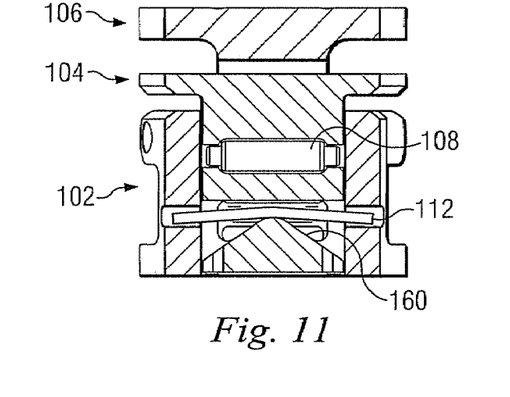
FIG. 11 is a sectional pictorial illustration taken along line 11-11 in FIG. 9.
Figure 12:
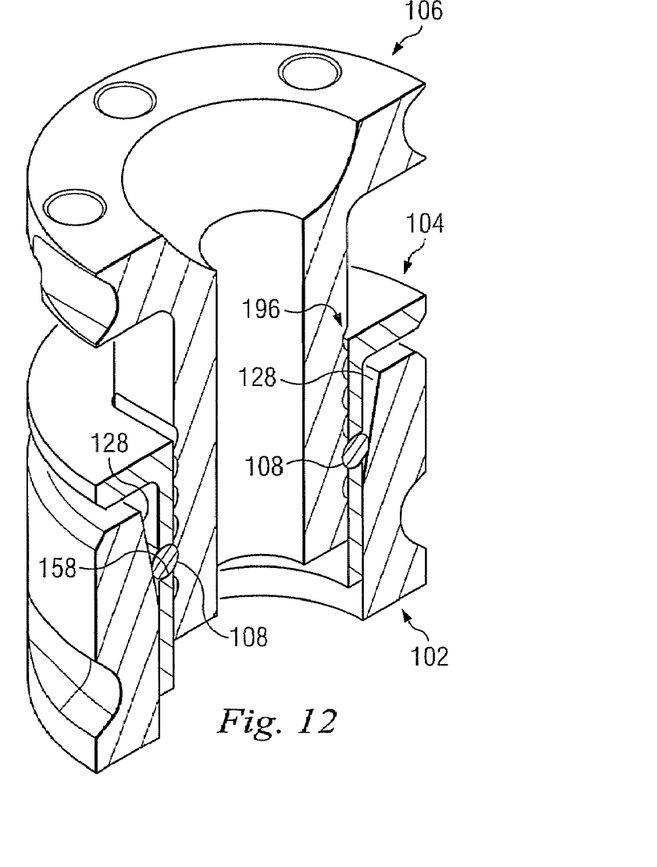
FIG. 12 is a sectional pictorial illustration of an exemplary locking arrangement usable with the implant of FIG. 2.

Operability of the implant 100 will be described with reference to FIGS. 9 through 12. FIG. 9 shows the implant 100 in an assembled condition. FIGS. 10 and 11 show cross-sectional views of the implant 100. FIG. 12 shows one model of components used to illustrate the functionality of the locking mechanism of the implant 100.

Referring now to the cross-sectional view in FIG. 10, the peg 110 is shown extending through the base 102, the locker 104, and into the post 106. As can be seen, the peg slot 164 in the locker 104 allows the locker 104 to move along the longitudinal axis L of the implant 100 relative to the base 102. Likewise, the peg slot 192 in the post 106 allows additional movement of the post 106 relative to the base 102. In this manner, the peg 110 may maintain the components of the implant 100 together, while at the same time allowing them to expand longitudinally to increase and decrease the overall implant height.

FIG. 11 is a cross-sectional view through the biasing element 112 and through the locking element 108. The locking element 108 is maintained in its location by the locking element receiver 158 of the locker 104. As shown in FIG. 11, the biasing element 112 cooperates with the base 102 and the biasing member support 160 of the locker 104 to limit the axial movement of the locker 104 relative to the base 102. The biasing element 112 provides a continuous biasing force against the locker 104 to maintain the locker 104 in a position that locks the height of the implant.

FIG. 12 shows the relationship of the locking element 108 with the base 102, the locker 104, and the post 106, according to one embodiment of the implant. The locking element 108 is disposed in the locking element receiver 158, and protrudes through the receiver 158 such that the locking element 108 is selectively in contact with both the base 102 and the post 106.

In use, when the locker 104 is raised relative to the base 102, the locking element 108 also raised relative to the base 102. Because the base 102 has a tapered section 128, upward movement of the locking element 108 relative to the base may provide free space for the locking element 108 to move away from the post 214. This may be referred to as an unlocked condition, allowing the post 214 to slide freely to either increase or decrease the overall height of the implant 100. Once the desired height is achieved, the locker 104 may be moved downward relative to the base 102, wedging the locking element 108 between the tapered surface 128 of the base 102 and the post 106. So doing locks the overall height of the implant at its desired height. This may be referred to as a locked condition. The roughened surface features, such as the scallops, of the post 106 may provide a locking location for the locking element 108 and may reduce slippage between the locking element 108 and the post 106.

In the embodiment shown, the overall height of the implant 100 can be increased simply by raising the post 106 relative to the base 104. So doing may force the locking element 108 to move upwardly along the tapered section 128 to the unlocked condition, thereby allowing the implant height to be increased without requiring any separate attention to the locker 104. This also allows the locking element 108 to freely engage and disengage the roughened features of the locking surface 196. Accordingly, in some embodiments such as those shown having the scalloped surface features, during expansion, an audible clicking may be generated as the locking element 108 moves past and falls into each scalloped feature of the locking surface 196. In some embodiments, the locker 104 and the locking element 108 are configured to require manual or separate displacement of the locker 104 and the locking element 108 to reduce the overall height of the implant 100.

In the embodiment shown, the locking element 108 is a cylindrical rod that distributes its locking force over a wide surface area and in the embodiment shown over the entire width of the post 106. Accordingly, the locking element 108 contacts the post 106 along a contact line transverse to the longitudinal axis L of the implant 100, rather than at a single point. Because of this, the implant is less conducive to undesired slipping. It should be noted that the scalloped surface on the post 106 is optional and the post 106 may include other roughened features, indentations or elements that increase the friction between the locking element and the post.

In the embodiment shown, the implant 100 includes symmetrically locking features, including opposed tapered surfaces on the base 102, two locking elements 108 in two opposed receiving apertures 158, and two opposite locking surfaces 196. This symmetry may aid expansion and collapse of the implant by substantially equalizing the forces required at each side of the implant to expand or collapse it, providing a better level of control to the physician placing or removing the implant.

During implantation, the implant 100 may be gripped with a surgical instrument at instrument receiving features of the base 102 and at the instrument receiving grips 200 of the post 106. In its smallest condition, the implant may be introduced to a patient through the smallest possible incision. In one exemplary embodiment, the implant 100 may be introduced between two bone structures, such as adjacent vertebral bodies, such as the vertebral bodies V2 and V4 in FIG. 1, replacing the vertebral body V3 along with the discs D2 and D3. Once positioned between the adjacent bone structures, the implant 100 may be distracted to increase the overall implant height. Using the instruments, the post 106 is longitudinally displaced relative to the base 102. In so doing, the post 106 frictionally acts on the locking element 108 to raise it relative to the base 102, along the tapered section 128. Once a desired height is achieved, the base 102 and post 106 are released. The continuous biasing force of the biasing member 112 acting on the locker 104 draws the locker 104 and the locking element 108 into a locking condition, where the locking element is wedged between the tapered section 128 and the locking surface 196 of the post 106. This compressive force locks the implant 100 against further decreases in the overall height. Once expanded, an implanting physician may introduce optional bone growth promoters into the base 102 or post 106 through the vascularization aperture 136 and the vascularization holes 194, respectively.

If it later becomes necessary to remove the implant, the locker flange 157 may be raised relative to the base 102 to remove the locking element 108 from its wedged position. Once the locking element 108 is free to disengage the locking surface 196 of the post 106, the post 106 may collapse into the locker 104, and the implant 100 may be removed from the patient. Again, although described with reference to one locking element, it is understood that two or more locking elements may be includes to provide symmetry.

In the implantation method described above, some amount of the distraction force is used to overcome the biasing force of the biasing member 112. In some embodiments, the biasing member may be adjusted to provide a stronger biasing force to resist undesirable actuation of the implant once released. The stronger the biasing member, the greater the force required to deploy the device. However, in other implantation methods, the locker 104 may be separately raised relative to the base 102 to release the locking element prior to distracting the post 106 from the base 102. In this way, the complete distraction force may be used for distraction, rather than a portion being used to overcome the biasing force acting on the locker 104.

In yet other implantation methods, the implant may also be deployed by raising the center post 106 relative to the base 102 from the bottom end 182. In these embodiments, deploying instruments may attach to the post bottom end 182, such as at the bottom surface 183, or to features on the post 106 such as the vascularization apertures 194, and in addition, attach to the instrument receiving features 124 on the base 102. By moving the post 106 from the bottom end 182 (or the vascularization apertures 194) relative to the instrument receiving features 124, the distance between the bottom end 182 (or the vascularization apertures 194) and the instrument receiving features 124 decreases, while the overall height of the implant increases. Accordingly, during deployment, the gripping portions of the instrument move closer together (decreasing the instrument size), while the height of the implant increases. Because in this embodiment, the instrument does not grip at the ends of the implant, the implant can be deployed into a space or cavity where both ends of the implant are not directly accessible at the same time.

Although the implant 100 is described as being somewhat porous with vascularization apertures 136, 162, 190, 194, other embodiments include either more or less vascularization apertures. In some embodiments, the post is substantially solid such that while it is telescopically received within the locker and base, no material may be received within the post, or alternatively, with in the base.

Figure 13:
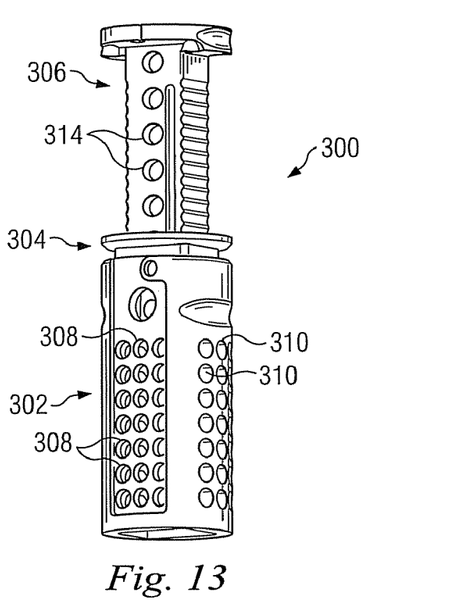
FIG. 13 is an elevation view of another exemplary embodiment of the present invention.
Figure 14:
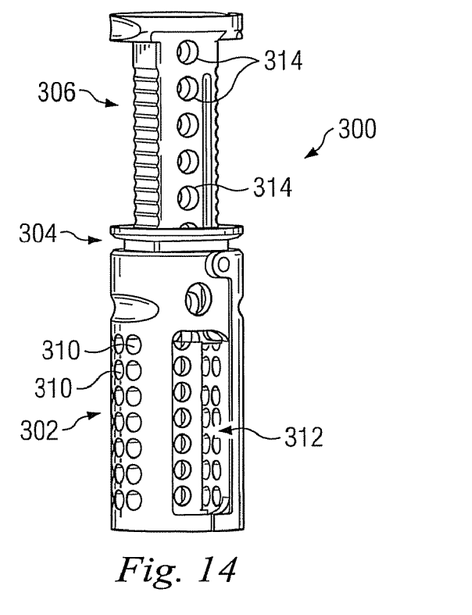
FIG. 14 is another elevation view of the exemplary embodiment of FIG. 13.

FIGS. 13 and 14 show an embodiment of another exemplary expandable implant 300 having additional vascularization openings. FIG. 13 shows a back side and FIG. 14 shows a front side. The implant 300 is similar to the implant 100 described above, including a base 302, a locker 304, and a post 306. In this embodiment, the heights of the base 302 and the post 306 are greater than those of the base 102 and post 106 described above. To accommodate grafting, tissue, or other material, the implant 300 includes rear vascularization openings 308, side vascularization openings 310, and at least one front access window 312. The rear and side openings 308, 310, as well as the access window 312, increase the porosity of the implant, promoting breathability and bone growth. The access window 312 is larger than the rear and side openings 308, 310 and provides access to the interior of the base 302. Accordingly, during implantation, a physician may introduce grafting material through the access window 312 to pack grafting material, tissue, or other material into the base 302. The larger size of the access window 312 simplifies the packing process, while the smaller size of the rear and side openings 308, 310 help reduce the opportunity for the material being packed to extrude from the rear or side openings. This may become important when the implant 300 is placed in a spine and the rear of the implant 100 is facing or located adjacent the spinal cord. Similarly, the larger size of the access window 312 may allow placement of large segments of grafting, tissue, or other material, while the smaller rear and side openings 308, 310 help contain the large segments within the base 302. The post 306 of the implant 300 also includes vascularization holes 314 similar to the vascularization holes 194 described above.

Figure 15:
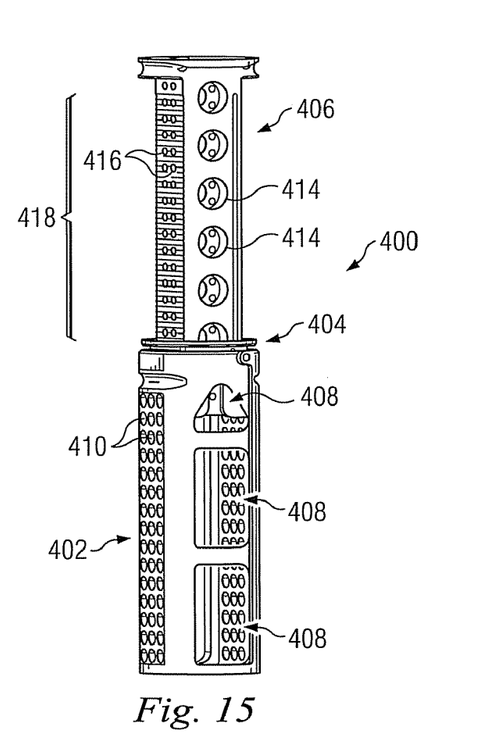
FIG. 15 is an elevation view of another exemplary embodiment of the present invention.
Figure 16:
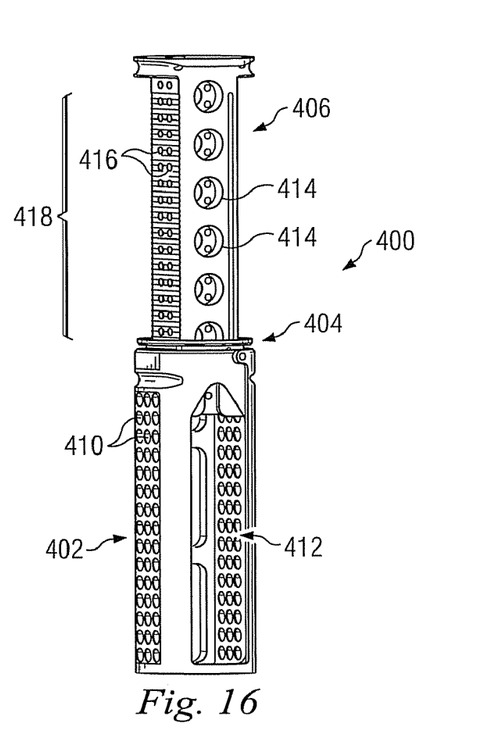
FIG. 16 is another elevation view of the exemplary embodiment of FIG. 15.

FIGS. 15 and 16 show another embodiment of an exemplary expandable implant 400. FIG. 15 shows a back side and FIG. 16 shows a front side. Again, the implant 400 is similar to the implant 100 described above, including a base 402, a locker 404, and a post 406. To accommodate grafting, tissue, or other material, the implant 400 includes rear vascularization openings 408, side vascularization openings 410, and front access windows 412 that increase the porosity of the implant, promoting breathability and bone growth. As described above, the access window 412 is larger than the rear and side openings 408, 410 and provides access to the interior of the base 402. In this embodiment, the rear openings 408 are larger than the side openings 410. Nevertheless, in this embodiment, the rear openings 408 are smaller than the access window 412. As can be seen, in this embodiment, the base 402 includes three rear openings 408.

The post 406 of the implant 400 also includes vascularization holes 414 similar to the vascularization holes 194 described above. In addition, the post 406 includes post openings 416 in a locking surface 418. The locking surface 418 may be similar to the locking surface 196 described above. The post openings 416 provide additional vascularization to the implant 400.

In the embodiments shown in FIGS. 13-16, the implants include only one access window. However, in other embodiments, the implants include more than one access window on the front side, while the rear and side openings are still maintained smaller than the front access windows. In other embodiments, the rear openings are smaller than the side openings. It also should be noted that the implant may include more or less than three rear openings, and the size of the openings may be determined in part based upon the size of the implant and based upon the size or amount of packing material anticipated.

While the post has been shown as telescopically received within the locker and the base, it will be appreciated that in a further embodiment the respective configuration is inverted such that a portion of the base is received within the post. Moreover, while a substantially cylindrical structure having rectangular bores has been shown for the purposes of illustration, in alternative embodiments the tubular and rectangular shapes may take the form of a rectangle, square, ellipse, diamond, oval, D-shape or any shape desired to conform and substantially match the adjacent bone or the bone structure that is being replaced. As a result, the definition of tubular is not intended to be limited to cylindrical but is instead intended to cover all components that may be utilized to reduce the present invention.

While the present device has been described with respect to insertion between two vertebrae after removal of the intervening vertebrae and intervertebral disc, it is contemplated that the length of the device may be sized appropriate to span multiple vertebrae. Additionally, the device may find application in other orthopedic areas and the size and shape of the device may be made to substantially match the implantation site. For example, while the present embodiment has been illustrated as a substantially cylindrical device, it is contemplated that in certain spinal applications it is desirable that the device have a substantially D shaped cross-section as viewed from top to bottom such that the anterior portion of the device has an exterior convexly curved surface matching the anterior of the vertebral body while the posterior portion of the device is substantially flat or concave allowing it to be positioned closer to the spinal canal without protruding into the spinal canal.

Embodiments of the implant in whole or in part may be constructed of biocompatible materials of various types. Examples of implant materials include, but are not limited to, non-reinforced polymers, carbon-reinforced polymer composites, PEEK and PEEK composites, shape-memory alloys, titanium, titanium alloys, cobalt chrome alloys, stainless steel, ceramics and combinations thereof. In some embodiments, the locking elements 108 are formed or cobalt chrome and the base 102, locker 104, and post 106 are formed of titanium.

If the implant is made from radiolucent material, radiographic markers can be located on the implant to provide the ability to monitor and determine radiographically or fluoroscopically the location of the implant in the spinal disc space. In some embodiments, radiographic markers are placed to show the location of the locking elements relative to the post and base.

In some embodiments, the implant or individual components of the implant are constructed of solid sections of bone or other tissues. In other embodiments, the implant is constructed of planks of bone that are assembled into a final configuration. The implant may be constructed of planks of bone that are assembled along horizontal or vertical planes through one or more longitudinal axes of the implant. In some embodiments, a cavity is cut or constructed through the implant. The cavity may be useful to contain grafting materials. Tissue materials include, but are not limited to, synthetic or natural autograft, allograft or xenograft, and may be resorbable or non-resorbable in nature. Examples of other tissue materials include, but are not limited to, hard tissues, connective tissues, demineralized bone matrix and combinations thereof. Examples of resorbable materials that may be used include, but are not limited to, polylactide, polyglycolide, tyrosine-derived polycarbonate, polyanhydride, polyorthoester, polyphosphazene, calcium phosphate, hydroxyapatite, bioactive glass, and combinations thereof. Implant may be solid, porous, spongy, perforated, drilled, and/or open.

In some circumstances, it is advantageous to pack all or a portion of the interior and/or periphery of the implant with a suitable osteogenetic material or therapeutic composition. Osteogenic materials include, without limitation, autograft, allograft, xenograft, demineralized bone, synthetic and natural bone graft substitutes, such as bioceramics and polymers, and osteoinductive factors. A separate carrier to hold materials within the device can also be used. These carriers can include collagen-based carriers, bioceramic materials, such as BIOGLASS®, hydroxyapatite and calcium phosphate compositions. The carrier material may be provided in the form of a sponge, a block, folded sheet, putty, paste, graft material or other suitable form. The osteogenetic compositions may include an effective amount of a bone morphogenetic protein, transforming growth factor β1, insulin-like growth factor 1, platelet-derived growth factor, fibroblast growth factor, LIM mineralization protein (LMP), and combinations thereof or other therapeutic or infection resistant agents, separately or held within a suitable carrier material. A technique of an embodiment of the invention is to first pack the interior of an unexpanded implant with material and then place one or both end members if desired.

Access to the surgical site may be through any surgical approach that will allow adequate visualization and/or manipulation of the bone structures. Example surgical approaches include, but are not limited to, any one or combination of anterior, antero-lateral, posterior, postero-lateral, transforaminal, and/or far lateral approaches. Implant insertion can occur through a single pathway or through multiple pathways, or through multiple pathways to multiple levels of the spinal column. Minimally invasive techniques employing instruments and implants are also contemplated.

It is understood that all spatial references, such as "top," "inner," "outer," "bottom," "left," "right," "anterior," "posterior," "superior," "inferior," "medial," "lateral," "upper," and "lower" are for illustrative purposes only and can be varied within the scope of the disclosure.

FIG. 1 illustrates four vertebrae, V1-V4, of a typical lumbar spine and three spinal discs, D1-D3. While embodiments of the invention may be applied to the lumbar spinal region, embodiments may also be applied to the cervical or thoracic spine or between other bone structures.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. An expandable medical implant for supporting bone structures, the implant having an overall implant height adjustable along a longitudinal axis, the implant comprising:
   an outer member being configured to cooperatively engage a first bone structure;
   an inner member receivable in the outer member and movable relative to the outer member to increase and decrease the overall implant height, the inner member being configured to cooperatively engage a second bone structure,
   wherein one of the outer and inner members includes a tapered surface and the other of the outer and inner members includes a scalloped roughened locking surface;
   and a locking element disposed between the tapered surface and the roughened locking surface, the tapered surface being longitudinally movable relative to the locking element to shift the locking element in a direction transverse to the longitudinal axis into engagement with the roughened locking surface to inhibit a decrease in the overall implant height.

2. The expandable implant of claim 1, wherein the outer member includes an inner surface forming the tapered surface and wherein the inner member includes the roughened locking surface.

3. The expandable implant of claim 1, further including a locker member disposed between the inner and outer member, the locker member including a receiving aperture containing the locking element.

4. The expandable implant of claim 3, wherein the locker member is configured to act on the locking element to affect the position of the locking element relative to the tapered surface, and wherein the tapered surface is configured to affect the position of the locking element relative to the roughened locking surface.

5. The expandable implant of claim 3, wherein the locker member and the locking element are movable relative to the tapered surface between a locked condition and a free condition.

6. The expandable implant of claim 5, further including a biasing member configured to bias the locker member toward the locked condition.

7. The expandable implant of claim 6, wherein the biasing member is a leaf spring.

8. The expandable implant of claim 1, wherein the locking element is substantially cylindrical.

9. The expandable implant of claim 8, wherein the locking element contacts the roughened locking surface along a line extending transverse to the longitudinal axis of the implant.

10. The expandable implant of claim 1, including two locking elements disposed between the inner and outer members at opposing sides of the inner member.

11. The expandable implant of claim 1, wherein the roughened locking surface of the inner member is a scalloped surface.

12. The expandable implant of claim 11, wherein the scalloped surface is formed of increments less than 1 mm apart.

13. The expandable implant of claim 1, wherein the inner member has a substantially rectangular cross section, and the roughened locking surface is formed on at least one side of the rectangle.

14. The expandable implant of claim 1, wherein at least one of the inner and outer members includes vascularization openings formed on opposing sides of the implant.

15. The expandable implant of claim 14, wherein the vascularization openings on one opposing side are larger than the vascularization openings on the other opposing side.

16. The expandable implant of claim 1, wherein the roughened locking surface includes at least one vascularization opening formed therein.

17. An expandable medical implant for supporting bone structures, the implant having an overall implant height adjustable along a longitudinal axis, the implant comprising:
    an outer member having an inner surface and being configured to cooperatively engage a first bone structure;
    an inner member receivable in the outer member and movable relative to the outer member to increase and decrease the overall implant height; the inner member having a scalloped roughened locking surface and being configured to cooperatively engage a second bone structure; and
    a locking element disposed between the inner surface of the outer member and the scalloped roughened locking surface of the inner member, the locking element being movable by axial translation between a locked condition and an unlocked condition,
    and a biasing member operable to bias the locking element in a longitudinal direction toward the locked condition, the locking element being disposed to selectively engage the roughened locking surface to inhibit a decrease in the overall implant height.

18. The expandable implant of claim 17, further including a locker member disposed between the inner and outer member, the locker member including a receiving aperture containing the locking element.

19. The expandable implant of claim 18, wherein the locker member is configured to act on the locking element to affect the position of the locking element relative to the outer member, and wherein a tapered surface of the outer member is configured to affect the position of the locking element relative to the roughened locking surface of the inner member.

20. The expandable implant of claim 17, further including a leaf spring biasing member configured to bias the locker member toward the locked condition.

21. The expandable implant of claim 17, wherein the locking element is substantially cylindrical.

22. The expandable implant of claim 21, wherein the locking element contacts the roughened locking surface along a line extending transverse to the longitudinal axis of the implant.

23. The expandable implant of claim 17, including two locking elements disposed between the inner and outer members at opposing sides of the inner member.

24. The expandable implant of claim 23, wherein at least one of the inner and outer members includes vascularization openings formed on opposing sides of the implant, and wherein the vascularization openings on one opposing side are larger than the vascularization openings on the other opposing side.

25. The expandable implant of claim 17, wherein the scalloped surface is formed of increments less than 1 mm apart.

26. The expandable implant of claim 17, wherein the inner member has a substantially rectangular cross section, and the roughened locking surface is formed on at least one side of the rectangle.

27. The expandable implant of claim 17, wherein at least one of the inner and outer members includes vascularization openings formed on opposing sides of the implant, and wherein the vascularization openings on one opposing side are larger than the vascularization openings on the other opposing side.

28. An expandable medical implant for supporting bone structures, the implant having an overall implant height adjustable along a longitudinal axis, the implant comprising:
    an outer member having a tapered inner surface and being configured to cooperatively engage a first bone structure;
    a locker member receivable in the outer member and longitudinally movable relative to the outer member, the locker member including a receiving aperture;
    an inner member receivable in the locker member and movable relative to the locker member and the outer member to increase and decrease the overall implant height, the inner member having a scalloped surface and being configured to cooperatively engage a second bone structure; and
    a locking element disposed within the receiving aperture of the locker member, the locking element interfacing with the tapered inner surface of the outer member and the scalloped surface of the inner member, the tapered surface being longitudinally movable relative to the locking element to transversely shift the locking element into engagement with the scalloped surface to inhibit a decrease in the overall implant height.

29. The expandable implant of claim 28, wherein the locker member and the locking element are movable relative the outer member between a locked condition and a free condition.

30. The expandable implant of claim 29, further including a biasing member configured to bias the locker member toward the locked condition.

31. The expandable implant of claim 30, wherein the biasing member is a leaf spring.

32. The expandable implant of claim 28, wherein the locking element is substantially cylindrical.

33. The expandable implant of claim 32, wherein the locking element contacts the scalloped surface along a line extending transverse to the longitudinal axis.

34. The expandable implant of claim 28, including two locking elements disposed between the inner and outer members at opposing sides of the inner member.

* * * * *